US00PP25906P3

(12) United States Plant Patent
Danziger

(10) Patent No.: US PP25,906 P3
(45) Date of Patent: Sep. 15, 2015

(54) ***PETUNIA* PLANT NAMED 'DRAY67'**

(50) Latin Name: *Petunia sensu wijsman*
Varietal Denomination: DRAY67

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 12 days.

(21) Appl. No.: 13/986,306

(22) Filed: Apr. 19, 2013

(65) Prior Publication Data

US 2014/0317814 P1 Oct. 23, 2014

(51) Int. Cl.
*A01H 5/02* (2006.01)

(52) U.S. Cl.
USPC ..... Plt./356.18
CPC ..... *A01H 5/02* (2013.01)

(58) Field of Classification Search
USPC ..... Plt./356.18
CPC ..... A01H 5/02
See application file for complete search history.

(56) References Cited

PUBLICATIONS

Plants with restricted propagation, May 2014 (retrieved online Dec. 12, 2014).*
Harris Seeds, Sep. 25, 2012.*

* cited by examiner

*Primary Examiner* — Keith Robinson
(74) *Attorney, Agent, or Firm* — Cassandra Bright

(57) ABSTRACT

A new and distinct *Petunia* cultivar named 'DRAY67' is disclosed, characterized by large very dark purple flowers with vivid yellow stripes. The new variety is of medium vigor and moderately well branched. Plants of 'DRAY67' flower abundantly and form a mounded shape. The new variety is a *Petunia,* normally produced as an outdoor garden or container plant.

2 Drawing Sheets

Figure 1:
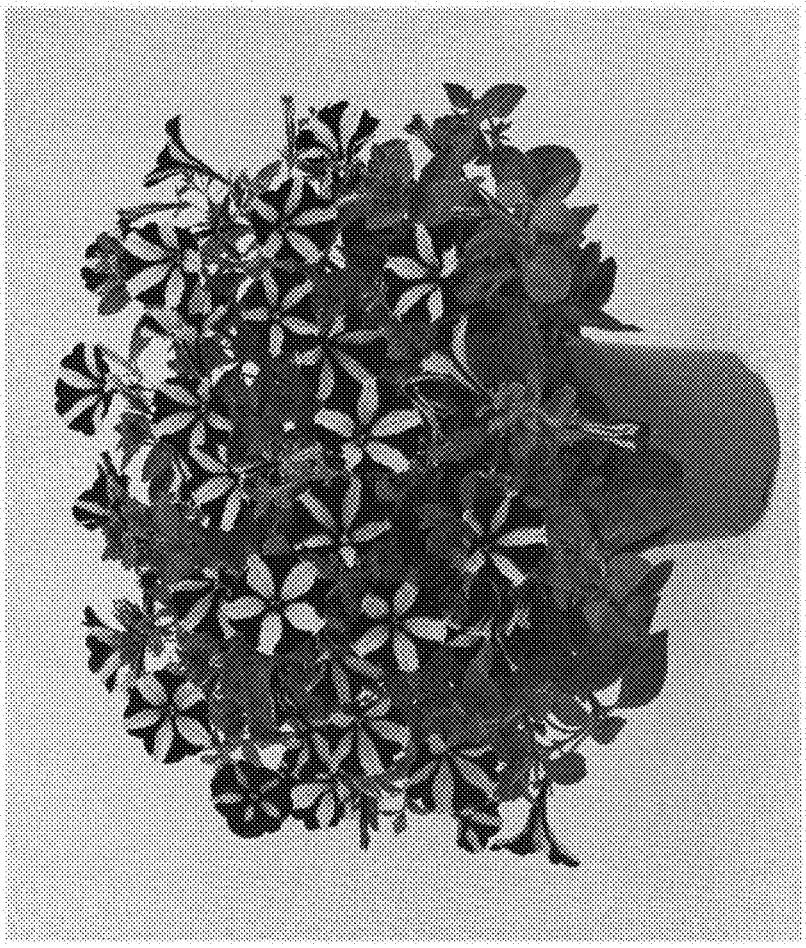

Latin name of the genus and species: *Petunia sensu wijsman.*

Variety denomination: 'DRAY67'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during September of 2010.

The seed parent is the unpatented non-commercial seedling variety referred to as *Petunia* '10-4176', containing the black gene described in utility patent U.S. Pat. No. 7,642,436. The pollen parent is the unpatented seedling variety referred to as *Petunia* '10-3945'. The new variety was discovered in May of 2011 by the inventor in a group of seedlings resulting from the 2010 crossing, in a research greenhouse in Moshav Mishmar Hashiva, Israel.

Asexual reproduction of the new cultivar has been performed by vegetative cuttings. This was first performed at a research greenhouse in Moshav Mishmar Hashiva, Israel in June of 2011 and has shown that the unique features of this cultivar are stable and reproduced true to type in more than 25 generations.

SUMMARY OF THE INVENTION

The cultivar 'DRAY67' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DRAY67' These characteristics in combination distinguish 'DRAY67' as a new and distinct *Petunia* cultivar:

1. Mounded plant shape.
2. Medium branched.
3. Flower color is very dark purple with vivid yellow stripes.
4. Flower size is large.
5. Abundant flowering.
6. Moderate vigor.

Plants of the new cultivar 'DRAY67' are similar to plants of the seed parent, *Petunia* '10-4176' in most horticultural characteristics, however, plants of the new cultivar 'DRAY67' are smaller, with less branches per plant than the seed parent. 'DRAY67' also produces an abundant quantity of large, very dark purple flowers with vivid yellow stripes, compared to the medium quantity of extra large, dark purple flowers with white stripes of the seed parent. Additionally 'DRAY67' exhibits a mounded plant habit compared to the semi upright plant habit of the seed parent '10-4176'.

Plants of the new cultivar 'DRAY67' are similar to plants of the pollen parent; *Petunia* '10-3945' in most horticultural characteristics, however, plants of the new cultivar 'DRAY67' produce an abundant quantity of large, very dark purple flowers with, vivid yellow stripes, compared to the medium quantity of medium yellow flowers of the seed parent. Additionally 'DRAY67' produces a mounded plant habit compared to the semi-upright plant habit of '10-3945'.

COMMERCIAL COMPARISON

Plants of the new cultivar 'DRAY67' are comparable to the variety *Petunia* 'Balpephan' U.S. Plant Pat. No. 22,440, which contains the gene described in U.S. Pat. No. 7,642,436. The two *Petunia* varieties are similar in most horticultural characteristics; however, the new variety 'DRAY67' differs in producing an abundant quantity of very dark purple flowers with vivid yellow stripes, compared to the larger purple flowers with less vivid yellow stripes of the comparator 'Balpephan'. Additionally 'DRAY67' produces elliptic shaped leaves, whereas leaves of comparator 'Balpephan' are of an ovate shape. The yellow striping found on the comparator 'Balpephan' is wider than the striping found on flowers of 'DRAY67'. Additionally 'DRAY67' produces flowers with a flat interior aspect compared to the curved, rolled interior of flowers of comparator 'Balpephan'.

Plants of the new cultivar 'DRAY67' can also be compared to the commercial variety *Petunia* 'Balpepin' U.S. Plant Pat. No. 22,414, which contains the gene described in U.S. Pat. No. 7,642,436. These varieties are similar in most horticultural characteristics; however 'DRAY67' produces abundant quantity of large, very dark purple flowers with vivid yellow stripes, compared to the larger purple with yellow-white striped flowers of comparator 'Balpepin'. 'DRAY67' produces a plant with medium width leaves compared to the wide leaves of comparator 'Balpepin'. Additionally 'DRAY67' produces a mounded plant form of medium vigor compared to the vigorous, semi-upright form of comparator 'Balpepin'.

BRIEF DESCRIPTION OF THE PHOTOGRAPHS

The accompanying photograph in FIG. 1 illustrates in full color a typical plant of 'DRAY67' grown in a greenhouse, in a 13 cm pot. Age of the plant photographed is approximately 3 months from a rooted cutting.

Figure 2:
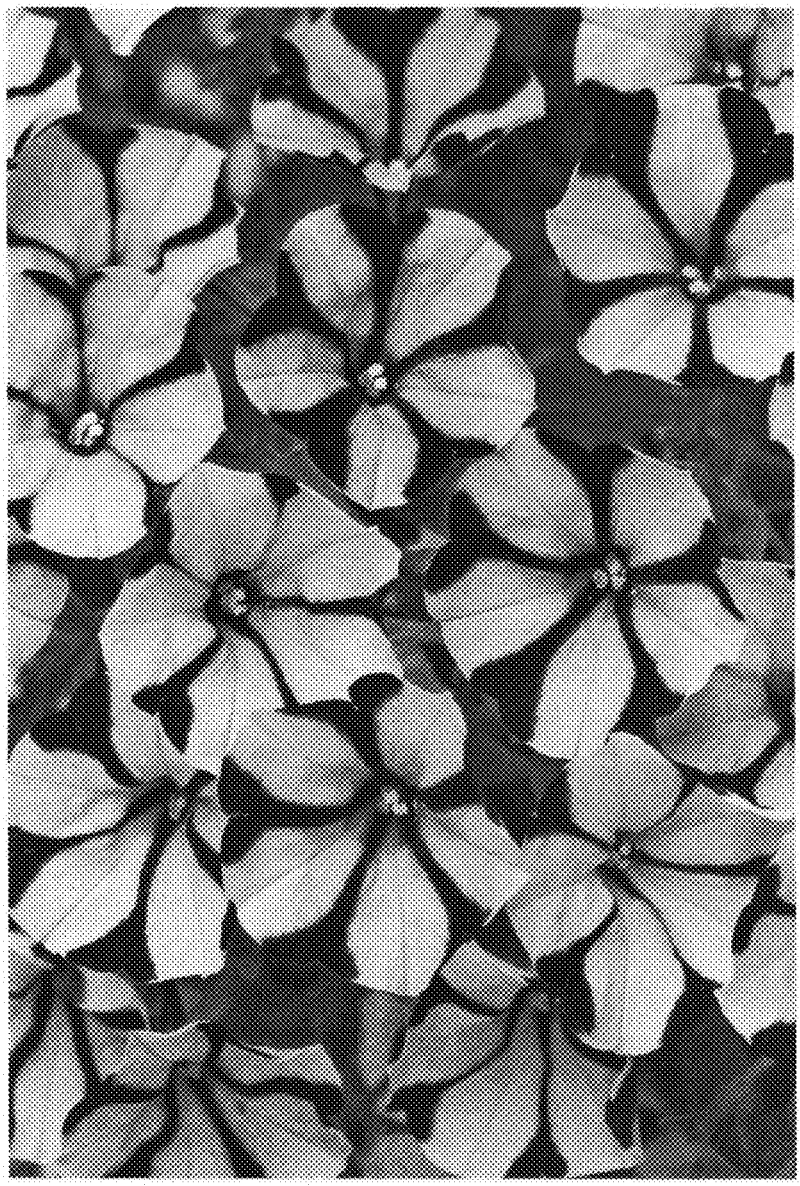

FIG. 2 illustrates in full color a close up of a typical bloom of 'DRAY67'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DRAY67' plants grown outdoors during, Spring, Summer, and Autumn in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu Wijsman* 'DRAY67'.

PROPAGATION

Time to initiate roots: About 10 to 14 days.
Root description: Fibrous.

PLANT

Age of plant described: Approximately 60 days from rooted cutting.
Pot size of plant described: 13 cm.
Growth habit: Mounded.
Height: To top of flowers about 24 cm.
Plant spread: 60 cm.
Growth rate: Moderately vigorous.
Branching characteristics: Moderately branched.
Quantity of primary lateral branches: 8.
Characteristics of primary lateral branches:
- *Form.*—Cylindrical.
- *Length.*—About 25 cm.
- *Diameter.*—About 0.4 cm.
- *Color.*—Green group 138A RHS.
- *Texture.*—Pubescent.
- *Strength.*—Strong, flexible.

Internode length: About 2.0 cm.

FOLIAGE

Leaf:
- *Arrangement.*—Opposite.
- *Quantity.*—Approximately 22 per branch.
- *Average length.*—6.0 cm.
- *Average width.*—2.8 cm.
- *Shape of blade.*—Elliptic.
- *Apex.*—Acute.
- *Base.*—Acute.
- *Margin.*—Entire.
- *Texture of top surface.*—Velvety, pubescent.
- *Texture of bottom surface.*—Velvety, semi-pubescent.
- *Aspect.*—90°.
- *Color.*—Young foliage upper side: Yellow-green group 146A RHS. Young foliage under side: Yellow-green group 146B RHS. Mature foliage upper side: Yellow-green group 146A RHS. Mature foliage under side: Yellow-green group 146B RHS.
- *Venation.*—Type: Pinnate. Venation color upper side: Yellow-green group 146B RHS. Venation color under side: Yellow-green group 146C RHS.
- *Petiole.*—Length: About 0.5 cm. Diameter: About 0.4 cm. Color: Yellow-green group 146A RHS. Texture: Velvety, pubescent.

FLOWER

Natural flowering season: Spring, Summer & Autumn.
Days to flowering from rooted cutting: About 30 day.
Inflorescence and flower type and habit: Axillary, single flower, salverform shape, erect, outwardly facing habit.
Rate of flower opening: 2 to 3 days from bud to fully opened flower.
Flower longevity on plant: 3 to 6 days.
Approximate quantity of flowers per plant: About 60.
Persistent or self-cleaning: Self-Cleaning.
Bud:
- *Shape.*—Tubular.
- *Length.*—About 4.5 cm.
- *Diameter.*—About 0.7 cm.
- *Color.*—Purple group N77A RHS.

Flower size:
- *Diameter.*—About 6.0 cm.
- *Flower tube length.*—About 4.0 cm.
- *Flower tube diameter at distal end.*—1.2 cm.
- *Flower tube diameter at proximal end.*—0.3 cm.

Petals:
- *Length from throat.*—About 2.5 cm.
- *Width.*—About 2.5 cm.
- *Quantity.*—5.
- *Texture.*—Velvety both upper and lower surfaces.
- *Apex.*—Blunt.
- *Margin.*—Entire.
- *Color.*—Background color: When opening: Upper surface: Violet-blue group N92A RHS. Lower surface:

Purple group 79A RHS. Fully opened: Upper surface: Violet-blue group N92A RHS. Lower surface: Purple group 79C RHS. Flower throat (inside): Violet-blue group N92A RHS. Flower throat, vein: Violet-blue group N92A RHS. Flower tube (outside): Purple group N77B RHS. Flower tube, vein: Yellow-green group 154B RHS. Fading: Petals fading to: Violet-blue group N92B RHS.

Description of the flower color striping: The flowers have five yellow stripes: Yellow-orange 14C RHS. Stripe width is usually about 8 to 12 mm. however some flowers on the same plant may have wider stripes, of about 15 to 19 mm. Others flowers on same plant may show less pronunciation of the yellow stripes, as five shorter triangles around the margin, or even five yellow dots around the margin.

*Calyx/sepals.*—Quantity per flower: 5. Shape: Linear. Length: About 1.2 cm. Corolla tube length: About 0.8 cm. Width: About 0.3 cm. Apex: Rounded. Base: Cuneate. Margin: Entire. Texture: Velvety both upper and lower surfaces. Color: Upper Surface: Yellow-green group 146A RHS. Lower Surface: Yellow-green group 146A RHS.

Peduncle:

*Length.*—About 3.0 cm.

*Diameter.*—About 0.1 cm.

*Color.*—Yellow-green group 146A RHS.

*Orientation.*—45° and straight.

Fragrance: None.

REPRODUCTIVE ORGANS

Stamens:

*Number.*—5.

*Filament length.*—About 2.5 cm.

Anthers:

*Shape.*—Rounded.

*Length.*—About 0.1 cm.

*Color.*—Yellow group 6D RHS.

Pollen:

*Color.*—Yellow group 6D RHS.

*Quantity.*—Much.

Pistil:

*Number.*—1.

*Length.*—About 2.2 cm.

*Style.*—Length: About 2.7 cm. Color: Yellow-green group 144C RHS.

*Stigma.*—Shape: Rounded. Color: Yellow-green group 146C RHS. Ovary Color: Yellow-green group 144B RHS.

OTHER CHARACTERISTICS

Seeds and fruits: About 60 near grey-brown N199B, rounded seeds of about 0.5 mm diameter, per one near Brown 200B conical capsule.

Disease/pest resistance: Neither resistance nor susceptibility to the normal diseases and pest of *Petunia* have been observed. Typical well known diseases include: *Botrytis cineria, Fusarium, Pythium, Phytophthora,* and *Rhizoctonia* species. Typical well known pests include: Leaf miners, spider mites, thrips and possibly caterpillars.

Temperature tolerance: From 5° to 40° C.

What is claimed is:

1. A new and distinct cultivar of *Petunia* plant named 'DRAY67' as herein illustrated and described.

* * * * *